(12) United States Patent
Okazaki et al.

(10) Patent No.: US 10,750,936 B2
(45) Date of Patent: Aug. 25, 2020

(54) PERICARDIAL-CAVITY OBSERVING METHOD

(71) Applicant: OLYMPUS CORPORATION, Tokyo (JP)

(72) Inventors: Yoshiro Okazaki, Tokyo (JP); Naoya Sugimoto, Tokyo (JP); Kazutoshi Kumagai, Kanagawa (JP); Shunji Takei, Tokyo (JP); Yusuke Nomura, Kanagawa (JP)

(73) Assignee: OLYMPUS CORPORATION, Tokyo (JP)

( * ) Notice: Subject to any disclaimer, the term of this patent is extended or adjusted under 35 U.S.C. 154(b) by 523 days.

(21) Appl. No.: 15/801,370

(22) Filed: Nov. 2, 2017

(65) Prior Publication Data

US 2019/0125172 A1 May 2, 2019

(51) Int. Cl.
*A61B 1/00* (2006.01)
*A61B 1/313* (2006.01)
(Continued)

(52) U.S. Cl.
CPC ........ *A61B 1/00183* (2013.01); *A61B 1/0008* (2013.01); *A61B 1/0014* (2013.01); *A61B 1/00085* (2013.01); *A61B 1/00089* (2013.01); *A61B 1/00091* (2013.01); *A61B 1/00096* (2013.01); *A61B 1/00131* (2013.01); *A61B 1/00135* (2013.01); *A61B 1/00147* (2013.01); *A61B 1/018* (2013.01); *A61B 1/0125* (2013.01); *A61B 1/0615* (2013.01);
(Continued)

(58) Field of Classification Search
None
See application file for complete search history.

(56) References Cited

U.S. PATENT DOCUMENTS 5,336,252 A * 8/1994 Cohen ................... A61M 25/09
606/129
5,601,576 A * 2/1997 Garrison ............ A61B 17/0469
606/139

(Continued)

FOREIGN PATENT DOCUMENTS

EP 3 009 062 A1 4/2016
JP H11-313795 A 11/1999
(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

A pericardial-cavity observing method including: a step of inserting an endoscope sheath and an endoscope into a space between the heart and the pericardium; a step of disposing a protruding portion closer to the pericardium than an optical member is so that an angle that is formed between a centerline that passes through a center of the protruding portion and a center of the optical member and a tangent of the pericardium that passes through a foot of a perpendicular line drawn, from the center of the optical member of the endoscope, to the pericardium sagging down from the protruding portion toward the heart becomes greater than an angle formed between the centerline and an external common tangent of the protruding portion and the optical member; and a step of observing the heart by means of the endoscope.

11 Claims, 15 Drawing Sheets

(51) Int. Cl.
  *A61B 1/06* (2006.01)
  *A61B 1/012* (2006.01)
  *A61B 1/018* (2006.01)
  *A61B 1/32* (2006.01)

(52) U.S. Cl.
  CPC ............ *A61B 1/3137* (2013.01); *A61B 1/32* (2013.01); *A61B 1/00045* (2013.01); *A61B 1/00154* (2013.01)

(56) References Cited

U.S. PATENT DOCUMENTS

| | | | | |
|---|---|---|---|---|
| 6,237,605 | B1* | 5/2001 | Vaska | A61B 18/00 128/898 |
| 6,666,861 | B1* | 12/2003 | Grabek | A61B 18/1492 600/101 |
| 7,214,180 | B2* | 5/2007 | Chin | A61B 17/00008 600/37 |
| 7,749,157 | B2* | 7/2010 | Bertolero | A61B 1/12 600/114 |
| 8,900,123 | B2* | 12/2014 | Okazaki | A61B 1/0008 600/102 |
| 9,393,001 | B2* | 7/2016 | Miyoshi | A61B 1/01 |
| 2003/0212446 | A1* | 11/2003 | Kaplan | A61N 1/0587 607/129 |
| 2004/0064138 | A1 | 4/2004 | Grabek | |
| 2004/0087831 | A1* | 5/2004 | Michels | A61B 17/3423 600/114 |
| 2007/0129719 | A1* | 6/2007 | Kendale | A61B 1/00101 606/41 |
| 2010/0042108 | A1* | 2/2010 | Hibino | A61B 1/0051 606/129 |
| 2010/0240952 | A1* | 9/2010 | Okazaki | A61M 25/1011 600/109 |
| 2010/0280539 | A1* | 11/2010 | Miyoshi | A61B 1/0008 606/190 |
| 2011/0071342 | A1* | 3/2011 | Okazaki | A61B 17/3431 600/37 |
| 2011/0190584 | A1* | 8/2011 | Sugahara | A61B 17/12109 600/116 |
| 2012/0095434 | A1* | 4/2012 | Fung | A61B 17/3421 604/500 |
| 2014/0114127 | A1* | 4/2014 | Ikeda | A61B 1/0057 600/109 |
| 2016/0095500 | A1 | 4/2016 | Kumagai et al. | |
| 2017/0319233 | A1* | 11/2017 | Fonger | A61B 17/3421 |

FOREIGN PATENT DOCUMENTS

| | | |
|---|---|---|
| JP | 2001-258822 A | 9/2001 |
| JP | 2014-239739 A | 12/2014 |
| WO | 2016/203606 A1 | 12/2016 |

* cited by examiner

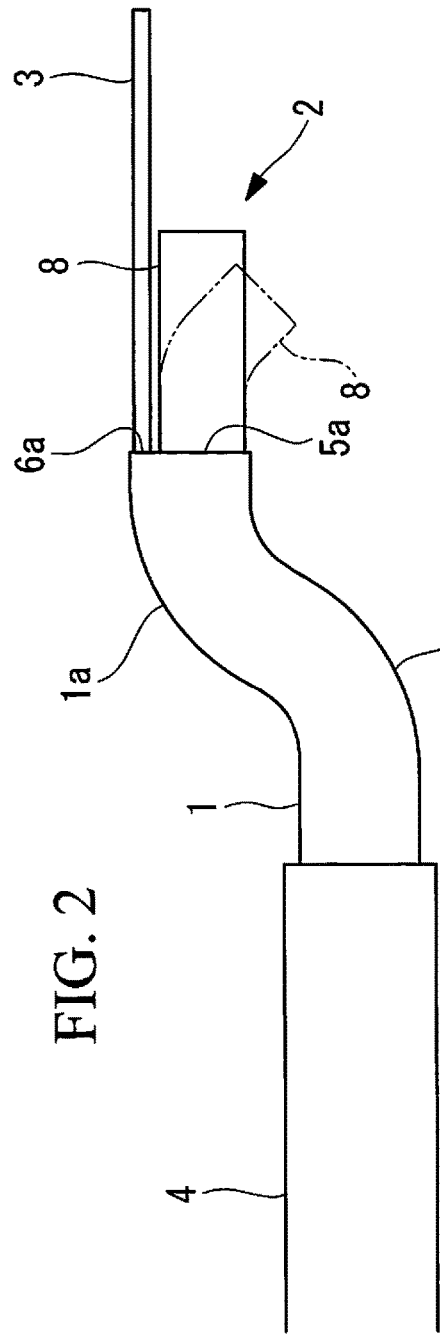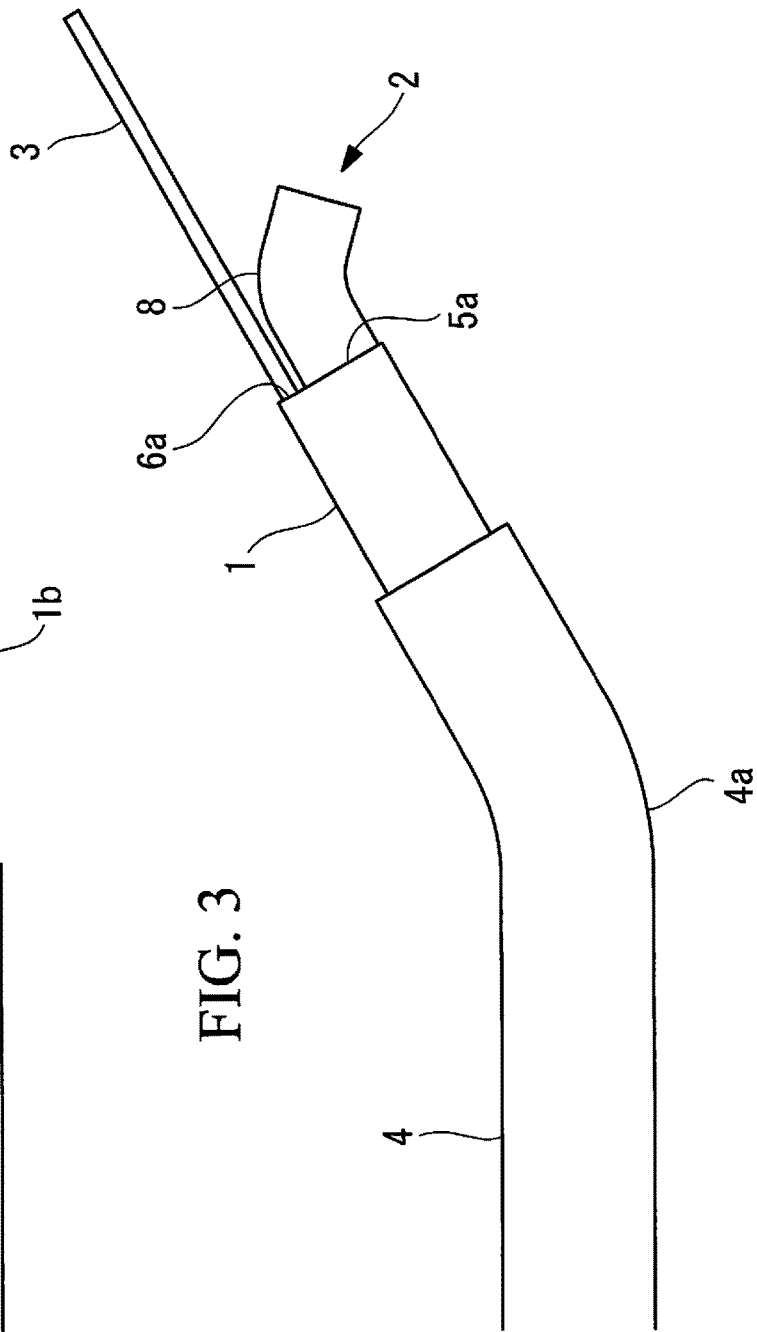

FIG. 9

| DESIGN VALUE / OBSERVATION CONDITIONS | RANGE | NORMAL STATE | φ IS MINIMUM | Z IS MAXIMUM |
|---|---|---|---|---|
| WIDTH OF WIRE W (mm) | 0.37~0.89 | 0.37 | 0.37 | 0.37 |
| SPACING BETWEEN ENDOSCOPE AND WIRE X (mm) | 0.15~1.00 | 0.15 | 0.15 | 0.15 |
| WIDTH OF OPTICAL MEMBER L (mm) | 2.0~4.0 | 2.0 | 2.0 | 2.0 |
| MAXIMUM DISTANCE BETWEEN HEART AND PERICARDIUM Z (mm) | 0~ | 20 | 20 | 35 OR GREATER |
| ANGLE BETWEEN CENTERLINE C AND TANGENT T2 β (deg) | ~90 | 46 | 36 OR LESS | 36 OR LESS |
| DIAMETER OF HEART φ (mm) | 50~250 | 100 | 58 OR LESS | 100 |
| OES PERICARDIUM INTERFERE WITH OBSERVATION? | | NO | YES | YES |

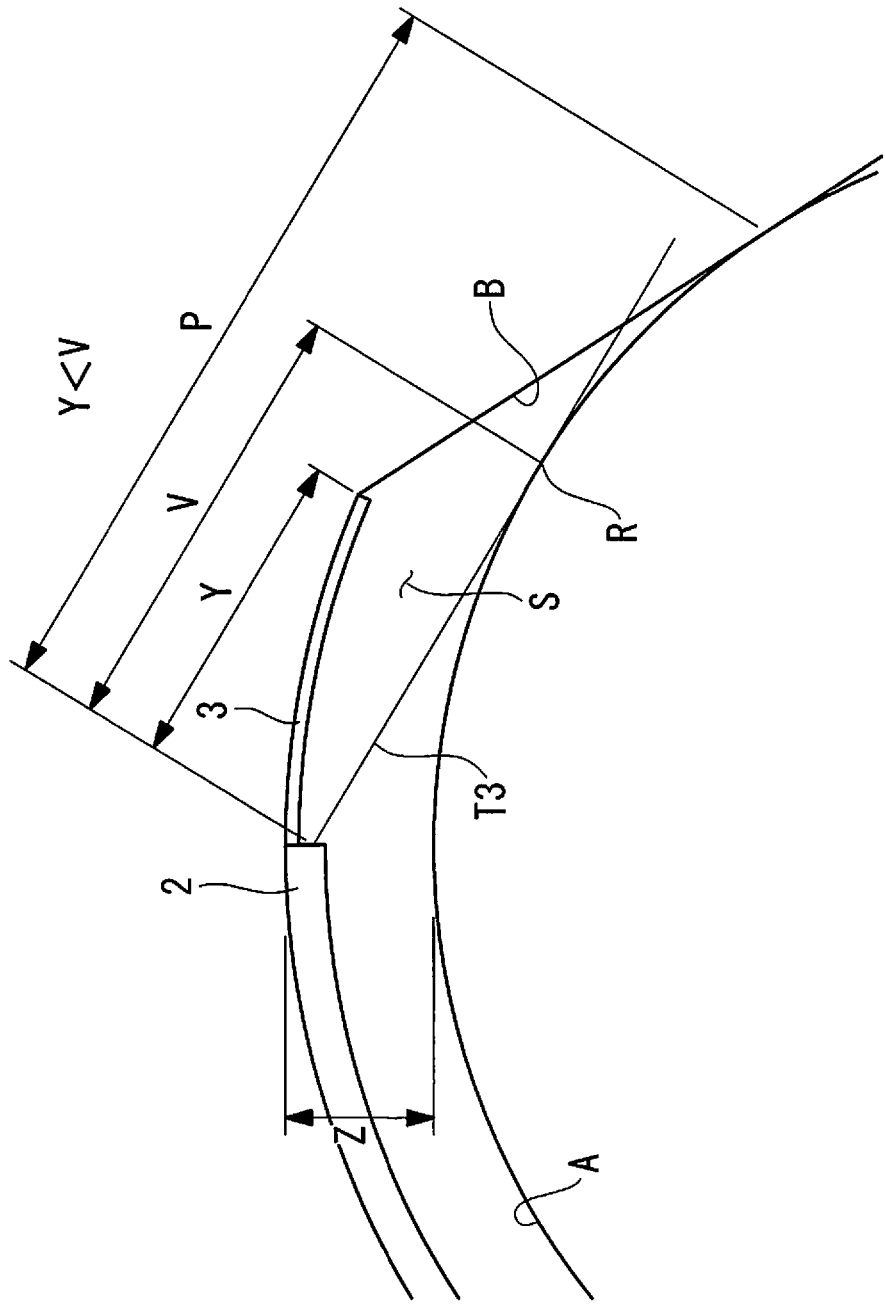

PERICARDIAL-CAVITY OBSERVING METHOD

TECHNICAL FIELD

The present invention relates to a pericardial-cavity observing method.

BACKGROUND ART

In the related art, there is a known method of observing a disease site in the pericardial cavity by inserting an endoscope thereinto from below the xiphoid process without performing thoracotomy (for example, see Patent Literature 1). At a distal-end surface of the endoscope, optical members for observing the interior of the pericardial cavity, such as an illumination lens and an objective lens, are disposed. Because the gap between the pericardium and the heart is small, in the case in which the method of Patent Literature 1 is used, the pericardium sags down in the area in front of the optical members of the endoscope, thus making it difficult to observe the interior of the pericardial cavity.

Therefore, in order to ensure a sufficient space for observing the interior of the pericardial cavity, an endoscope system provided, on the upper side of the endoscope, with a hood that protrudes farther forward than the distal-end surface of the endoscope has been proposed (for example, see Patent Literature 2). By lifting up the pericardium in a direction in which the pericardium is separated from the heart by using the hood, it is possible to ensure a sufficient space in the area in front of the distal-end surface of the endoscope, and thus, it is possible to perform bird's-eye-view observation of the heart by means of the endoscope. In order to realize less invasive surgery, it is preferable that the hood be a member that is smaller than the optical members of the endoscope, such as a guide wire.

CITATION LIST

Patent Literature

{PTL 1} US Patent Application, Publication No. 2004/0064138
{PTL 2} PCT International Publication No. WO 2016/203606

SUMMARY OF INVENTION

An aspect of the present invention is a pericardial-cavity observing method using an endoscope system provided with a tubular elongated endoscope sheath that has a lumen that passes therethrough in a longitudinal direction and that has a first radial direction and a second radial direction that are orthogonal to each other, a protruding portion that is disposed on one side of a distal-end opening of the lumen in the first radial direction and that protrudes from a distal-end surface of the endoscope sheath in the longitudinal direction, and an endoscope that has, at a distal end thereof, an optical member for observing an imaging subject and that is disposed in the lumen in a longitudinal direction thereof, wherein the protruding portion has a width that is smaller than that of the optical member in the second radial direction, the pericardial-cavity observing method including: a step of inserting the endoscope sheath and the endoscope into a space between a heart and a pericardium; a step of disposing the protruding portion closer to the pericardium than the optical member is; and a step of observing the heart by means of the endoscope, wherein, in the step of disposing the protruding portion, the protruding portion is disposed so that an angle that is formed between a centerline that passes through a center of the protruding portion and a center of the optical member and a tangent of the pericardium that passes through a foot of a perpendicular line drawn, from the center of the optical member, to the pericardium sagging down from the protruding portion toward the heart becomes greater than an angle formed between the centerline and an external common tangent of the protruding portion and the optical member.

BRIEF DESCRIPTION OF DRAWINGS

FIG. 2 is a diagram for explaining bending motions of first and second bending portions of an endoscope sheath.

FIG. 3 is a diagram for explaining a bending motion of a bending portion of an access sheath.

FIG. 9 is a table showing examples of design values of the endoscope system and conditions for observing the pericardial cavity.

FIG. 10B is a diagram for explaining the relationship between the maximum object distance and the protrusion length of the wire.

DESCRIPTION OF EMBODIMENT

A pericardial-cavity observing method according to an embodiment of the present invention will be described below with reference to the drawings.

Figure 1A:
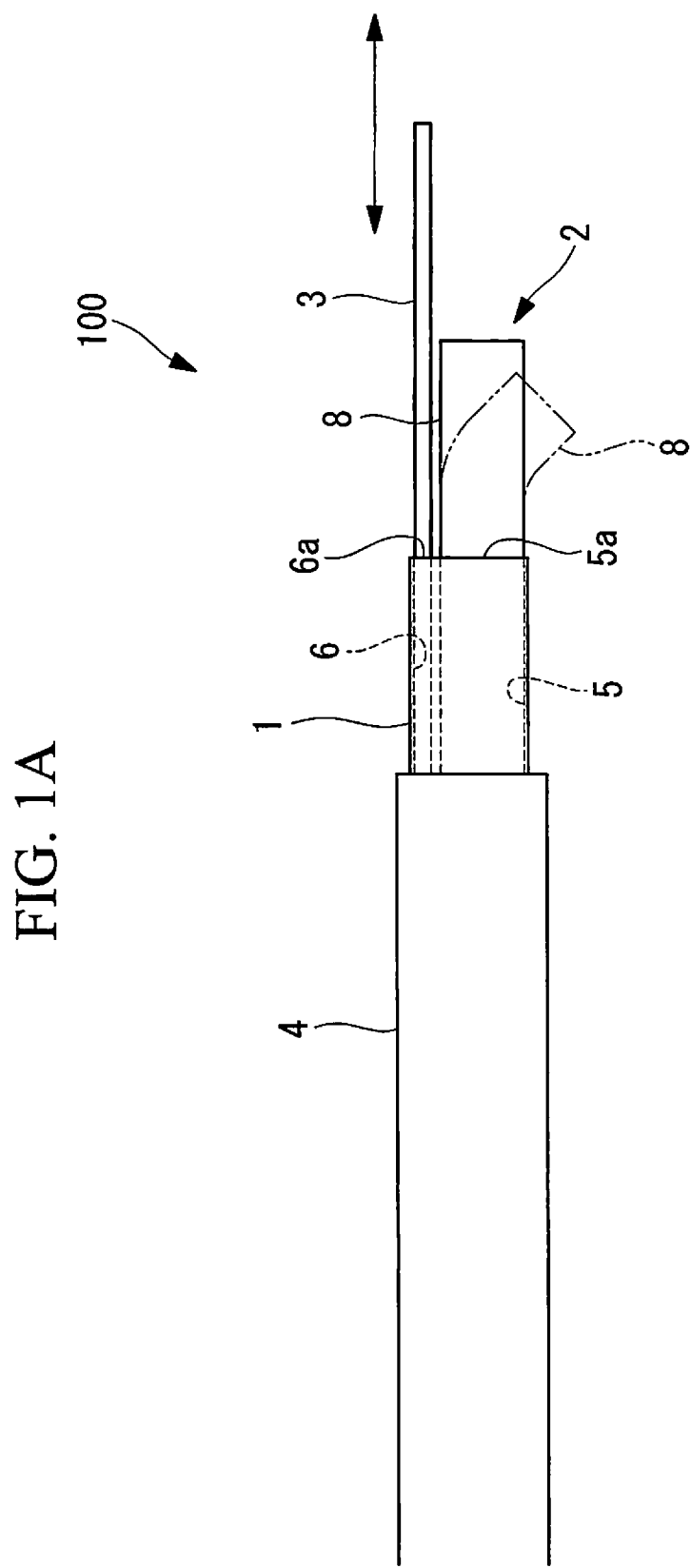
FIG. 1A is a configuration diagram of an endoscope system used in a pericardial-cavity observing method according to an embodiment of the present invention.
Figure 1B:
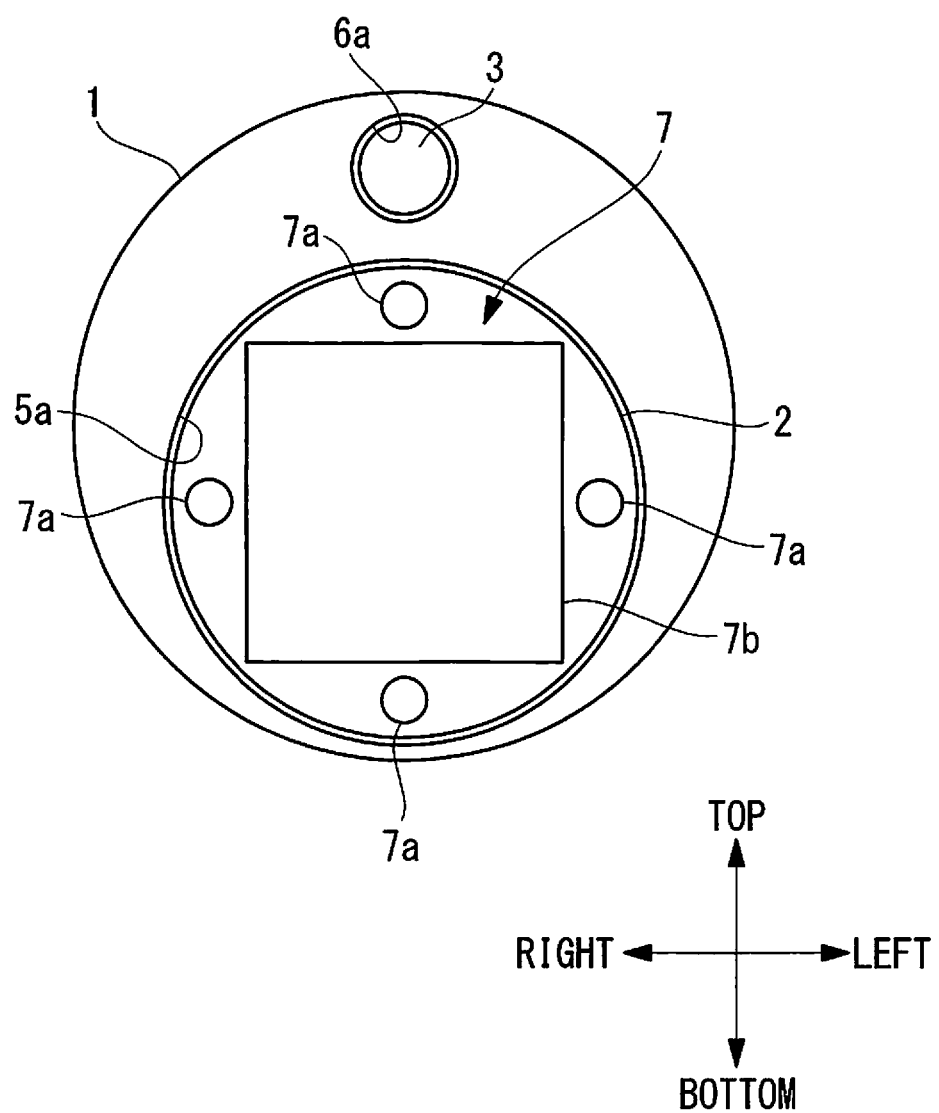
FIG. 1B is a front view as viewed from a distal-end side of the endoscope system in FIG. 1A.

The pericardial-cavity observing method according to this embodiment is a method of observing the interior of the pericardial cavity, particularly, a heart A, by using an endoscope system 100 shown in FIGS. 1A and 1B.

The endoscope system 100 is provided with: an elongated circular tubular endoscope sheath 1; an endoscope 2 that is inserted into the endoscope sheath 1; a wire (protruding portion) 3 that is protrudable from and retractable into a distal-end opening (opening portion) 6a in a distal-end surface of the endoscope sheath 1 in the longitudinal direction; and an elongated circular tubular access sheath 4 into which the endoscope sheath 1 is inserted.

The endoscope sheath 1 possesses flexibility that allows bending thereof in conformity to the shape of tissue in the body and can be inserted into the pericardial cavity. The endoscope sheath 1 has a lumen 5 that passes therethrough in the longitudinal direction and in which the endoscope 2 is disposed in the longitudinal direction, and a lumen 6 that passes therethrough in the longitudinal direction and in which the wire 3 is disposed in the longitudinal direction. The lumen 5 has an inner diameter that is greater than the outer diameter of the endoscope 2, and thus, it is possible to move the endoscope 2 in the longitudinal direction in the lumen 5 and to rotate the endoscope 2 about the longitudinal axis in the lumen 5. The lumen 6 has an inner diameter that is greater than the outer diameter of the wire 3, and thus, it is possible to move the wire 3 in the longitudinal direction in the lumen 6.

The endoscope sheath 1 has a top-to-bottom direction (first radial direction) and a left-to-right direction (second radial direction) that are radial directions that are orthogonal to the longitudinal axis and orthogonal to each other. The distal-end openings 5a and 6a of the lumens 5 and 6 in the distal-end surface of the endoscope sheath 1 are arranged in the top-to-bottom direction, and the distal-end opening 6a is positioned on the upper side of the distal-end opening 5a. As shown in FIG. 2, a distal-end portion of the endoscope sheath 1 may be provided with a first bending portion 1a that bends downward and a second bending portion 1b that is provided on the base-end side of the first bending portion 1a and that bends upward.

The endoscope 2 is a forward-viewing type endoscope and that is provided with: an optical member 7 provided at the distal end thereof to observe an area in front of the endoscope 2; and a bending portion 8 that is provided closer to the base end than the optical member 7 is.

As shown in FIG. 1B, the optical member 7 includes illumination lenses 7a from which illumination light is emitted toward an imaging subject facing the distal-end surface of the endoscope 2 and an objective lens 7b that forms an image by receiving light coming from the imaging subject, and the most-distal-end-side faces of the individual lenses 7a and 7b are disposed in the distal-end surface of the endoscope 2. The image of the imaging subject formed by the objective lens 7b is captured by an image sensor (not shown), and thus, an endoscope image is acquired. The acquired endoscope image is displayed on a monitor (not shown) connected to the endoscope 2.

The endoscope 2 has a top-to-bottom direction and a left-to-right direction that are radial directions orthogonal to the longitudinal axis and orthogonal to each other. The top-to-bottom direction and the left-to-right direction of the endoscope 2 correspond to the top-to-bottom direction and the left-to-right direction of the endoscope image, respectively. The bending portion 8 is bendable at least downward.

The wire 3 possesses a rigidity that allows the wire to maintain a substantially straight shape by resisting a force received from a pericardium B in the pericardial cavity while possessing flexibility that allows the wire to bend in conformity to the bent shape of the endoscope sheath 1. A base-end portion of the wire 3 is pulled outside the endoscope sheath 1 from a base-end opening of the lumen 6. By pulling and pushing the base-end portion of the wire 3 in the longitudinal direction, an operator can make the distal-end portion of the wire 3 retract into and protrude from the distal-end opening 6a.

Figure 4:
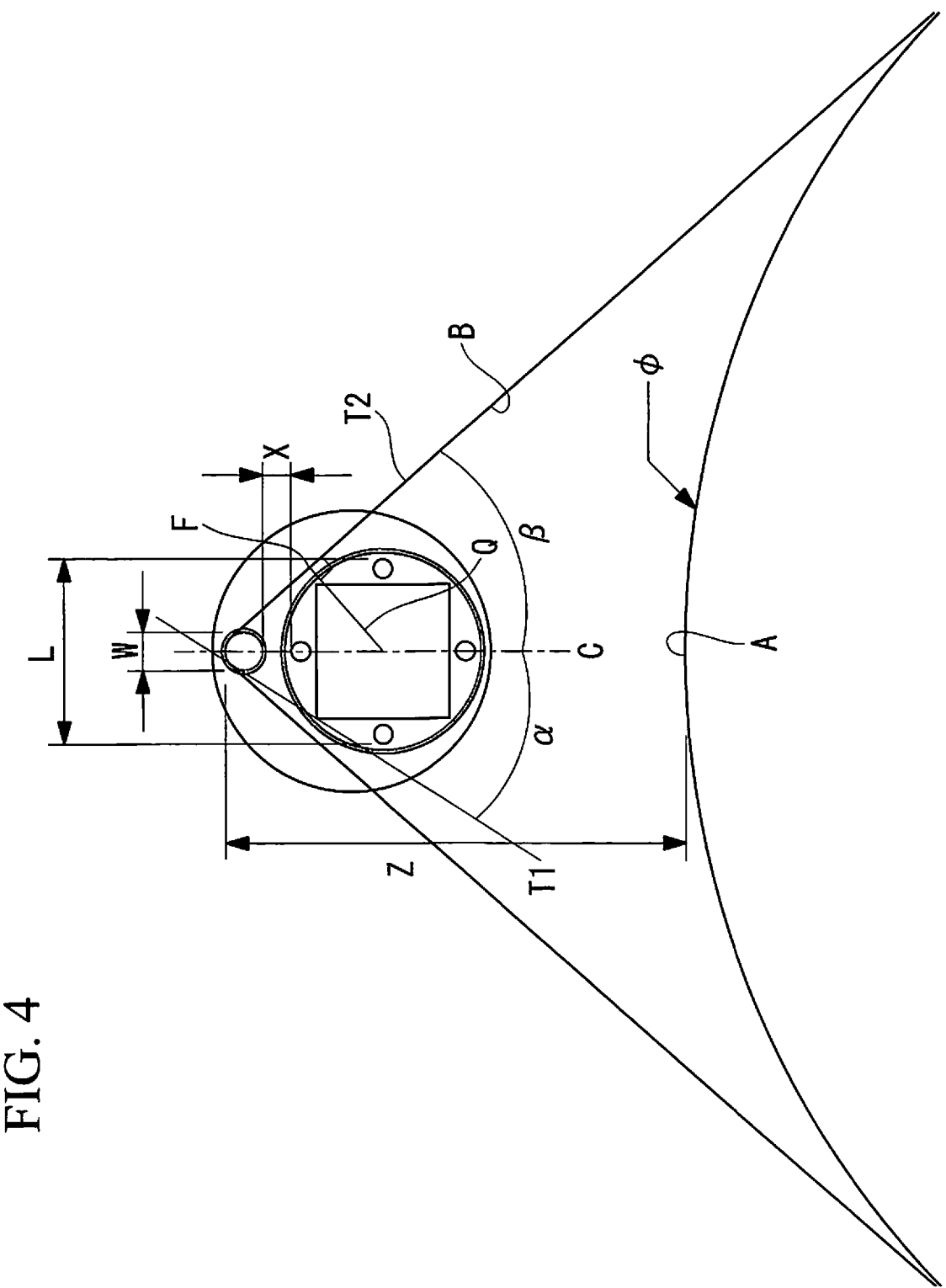
FIG. 4 is a front view of the endoscope system disposed in the pericardial cavity, and is a diagram for explaining geometric parameters of the endoscope sheath, the endoscope, a wire, the heart, and the pericardium.

FIG. 4 is a front view of the endoscope sheath 1 and the endoscope 2 disposed in the pericardial cavity. In FIG. 4, in order to avoid making the figure complicated, reference signs of the individual structures in the endoscope sheath 1 and the endoscope 2 are omitted.

An outer diameter W of the wire 3 in the left-to-right direction is equal to or greater than 0.3 mm. Although a wire 3 in which the transverse cross-sectional shape is a true circle is shown in the drawings referred to, the transverse cross-sectional shape of the wire 3 may be another shape, such as an ellipse or a polygon. A width L of the optical member 7 in the left-to-right direction is greater than the outer diameter W of the wire 3 and is equal to or greater than 2 mm. The width L is the width of the entire optical member 7 including the illumination lenses 7a and the objective lens 7b. A spacing X between the wire 3 and the optical member 7 in the top-to-bottom direction is equal to or greater than 0.15 mm.

The access sheath 4 has an inner diameter that is greater than the outer diameter of the endoscope sheath 1, and thus, it is possible to move the endoscope sheath 1 in the longitudinal direction in the access sheath 4 and to rotate the endoscope sheath 1 about the longitudinal axis in the access sheath 4. As shown in FIG. 3, the distal-end portion of the access sheath 4 may be provided with a bending portion 4a that is bendable in a direction that intersects the longitudinal direction.

Figure 5:
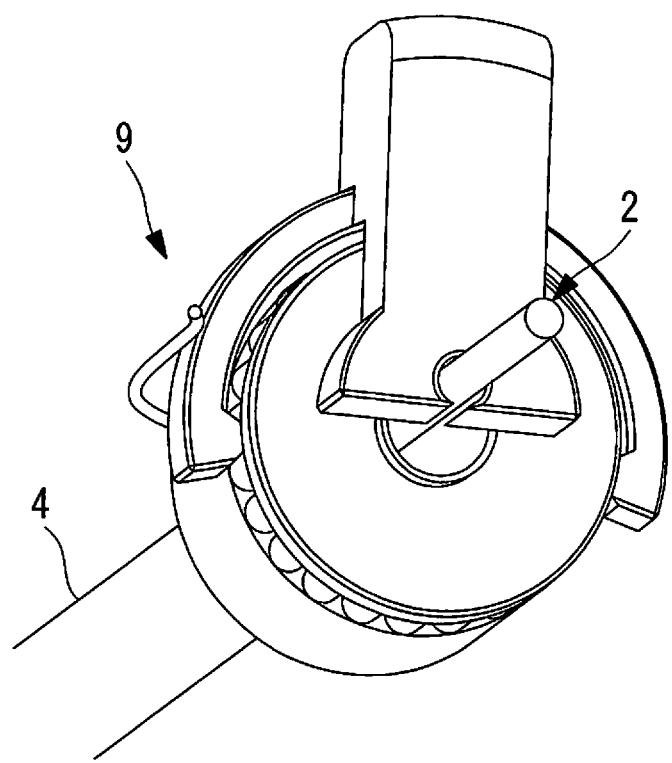
FIG. 5 is a diagram showing an example of an endoscope rotation-stopping mechanism.

It is preferable that the endoscope system 100 be provided with a rotation-stopping mechanism for the endoscope 2 that restricts the rotation of the endoscope 2 so that the endoscope 2 is not rotated about the longitudinal axis in the access sheath 4. The rotation-stopping mechanism for the endoscope 2 is, for example, as shown in FIG. 5, a securing device 9 that is attached to the base-end portion of the access sheath 4 and that secures the endoscope 2 to the access sheath 4 by holding the endoscope 2 at an intermediate position thereof in the longitudinal direction.

Figure 6:
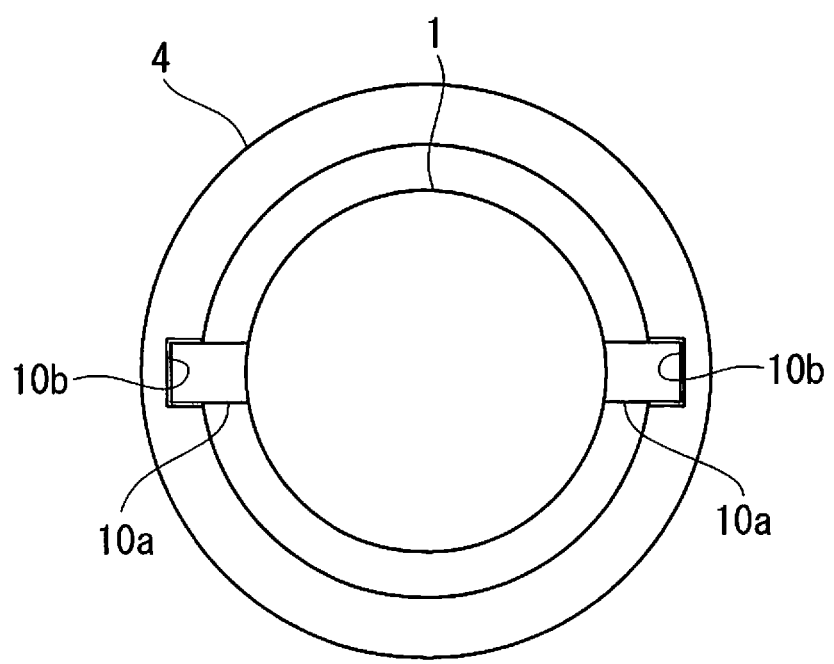
FIG. 6 is a diagram showing an example of an endoscope-sheath rotation-stopping mechanism.

In addition, it is preferable that the endoscope system 100 be provided with a rotation-stopping mechanism for the endoscope sheath 1 that restricts the rotation of the endoscope sheath 1 so that the endoscope sheath 1 is not rotated about the longitudinal axis in the access sheath 4. The rotation-stopping mechanism for the endoscope sheath 1 is formed of, for example, as shown in FIG. 6, a protrusion 10*a* that protrudes in a radial direction from a portion of an outer side surface of the endoscope sheath 1 in a circumferential direction, and a groove 10*b* that is formed on an inner surface of the access sheath 4 and that receives the protrusion 10*a* in a radial direction.

Next, the pericardial-cavity observing method employing the endoscope system 100 will be described.

The pericardial-cavity observing method includes: an inserting step of inserting the endoscope sheath 1 and the endoscope 2 into the pericardial cavity between the heart A and the pericardium B; a wire placing step of disposing the wire 3 closer to the pericardium B than the optical member 7 is; and an observing step of observing an observation target site (for example, the left atrial appendage) in the heart A by means of the endoscope 2.

Figure 7A:
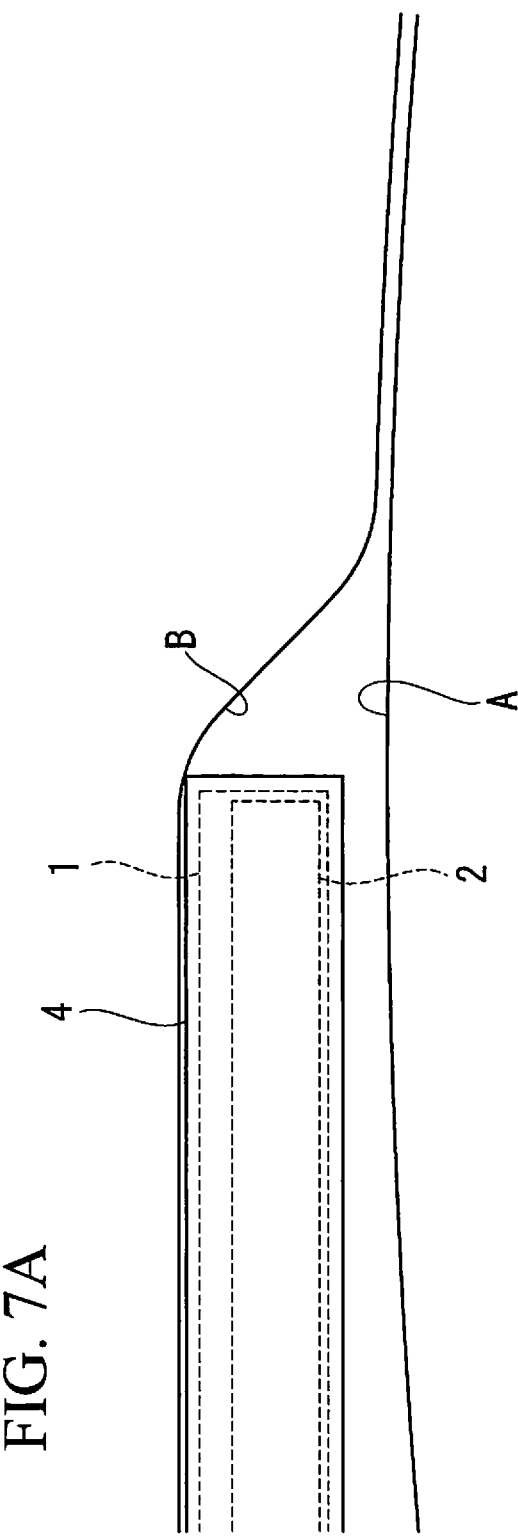
FIG. 7A is a diagram for explaining an inserting step of the pericardial-cavity observing method according to the embodiment of the present invention.

As shown in FIG. 7A, in the inserting step, the endoscope sheath 1 and the endoscope 2 in the lumen 5 of the endoscope sheath 1 are inserted into the pericardial cavity via the interior of the access sheath 4, which is disposed in the pericardial cavity from below the xiphoid process. Before the inserting step, the access sheath 4 is inserted into the pericardial cavity while checking the position of the access sheath 4 in the body by using, for example, an X-ray fluoroscopic image.

Next, the access sheath 4 is manipulated while observing the interior of the pericardial cavity by means of the endoscope 2 via the distal-end opening of the access sheath 4, and the distal end of the access sheath 4 is disposed in the vicinity of the observation target site. Next, the endoscope 2 is rotated about the longitudinal axis, and the orientation of the endoscope 2 about the longitudinal axis is adjusted so that the heart A is disposed on the lower side in the endoscope image and the pericardium B is disposed on the upper side thereof. Subsequently, the endoscope sheath 1 and the endoscope 2 are made to protrude from the distal end of the access sheath 4.

Next, as shown in FIG. 4, in the wire placing step, the wire 3 is disposed so that angles β become greater than angles α on the left and right sides of a centerline C when the endoscope sheath 1 and the endoscope 2 disposed between the heart A and the pericardium B are viewed from the distal end side in the longitudinal direction. The centerline C is a straight line that passes through the center of the wire 3 and the center of the optical member 7. The angle α is an angle that is formed between the centerline C and an external common tangent T1 of the wire 3 and the optical member 7. The angle R is an angle that is formed between the centerline C and a tangent T2 of the pericardium B that passes through a foot F of a perpendicular line Q that is drawn, from the center of the optical member 7, to the pericardium B sagging down from the wire 3 toward the heart A.

Specifically, in the wire placing step, first, the wire 3 is made to protrude from the distal-end opening 6*a* so that the distal-end portion of the wire 3 is observed in the endoscope image. By doing so, the distal end of the wire 3 is disposed at a position that is protruded farther out from the distal-end surface of the endoscope sheath 1 than the distal-end surface of the endoscope 2 is.

Figure 7B:
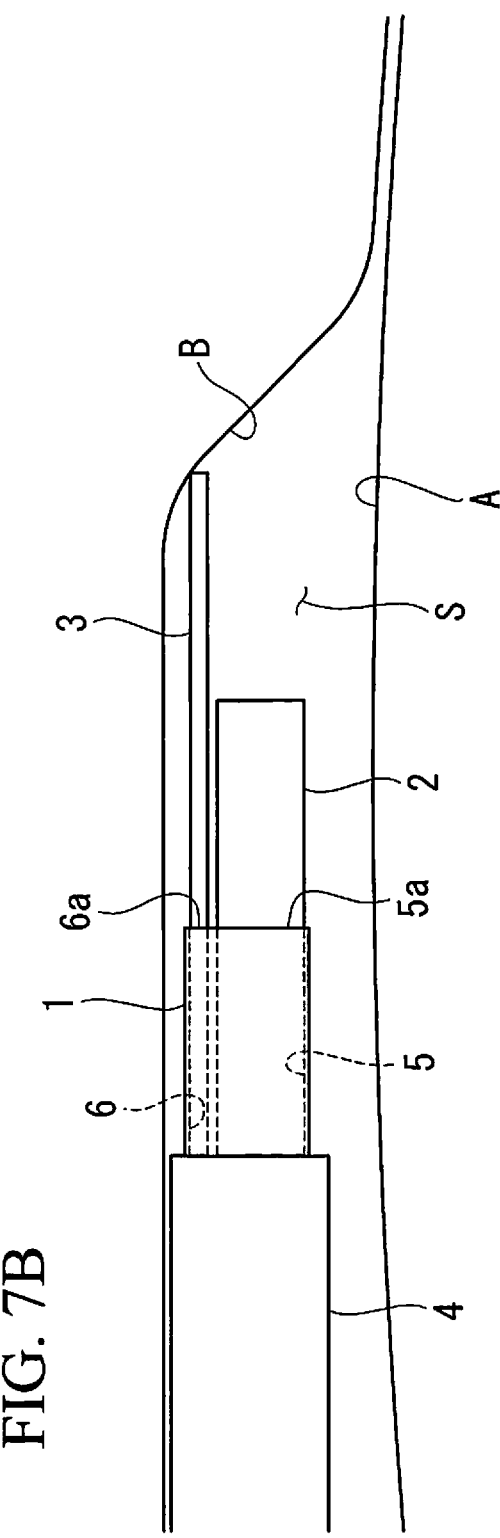
FIG. 7B is a diagram for explaining a wire placing step of the pericardial-cavity observing method according to the embodiment of the present invention.

Next, while maintaining the orientation of the endoscope 2, the endoscope sheath 1 is rotated about the longitudinal axis of the endoscope 2, and thus, the orientation of the endoscope sheath 1 is adjusted so as to dispose the wire 3 on the upper side in the endoscope image. By doing so, the wire 3 is disposed closer to the pericardium B than the optical member 7 is, and the pericardium B, the wire 3, the optical member 7, and the heart A are arranged in this order in the top-to-bottom direction of the endoscope 2. In this state, by means of the wire 3 that is disposed between the endoscope 2 and the pericardium B and that protrudes farther out than the distal-end surface of the endoscope 2, as shown in FIG. 7B, the pericardium B is lifted up in the direction in which the pericardium B is separated from the heart A in the area in front of the distal-end surface of the endoscope 2. If the angle β is greater than the angle α in the state shown in FIG. 7B, the wire placing step is terminated, and the procedure advances to the subsequent observing step.

Figure 8A:
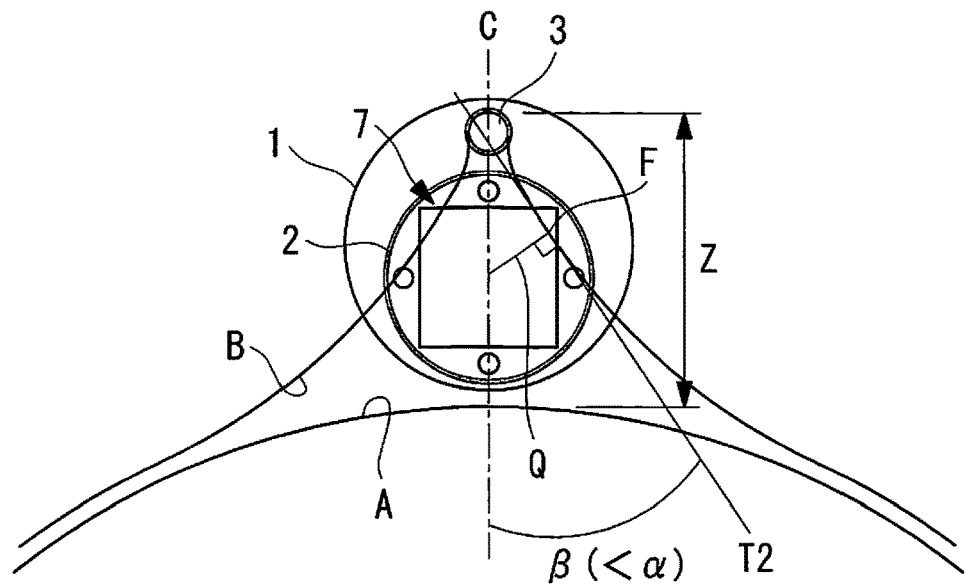
FIG. 8A is a diagram for explaining the wire placing step, and is a front view of the endoscope sheath and the endoscope disposed between the heart and the pericardium.

On the other hand, after adjusting the orientation of the endoscope sheath 1, as shown in FIG. 8A, if the pericardium B that sags down from the wire 3 toward the heart A covers the area in front of the optical member 7, and, if the angle β is still equal to or less than the angle α, subsequently, the wire 3 is moved upward (toward the pericardium B). By moving the wire 3 upward, a tensile force acts on the pericardium B that sags down from the wire 3 toward the heart A, and the pericardium B is moved in the left-to-right direction in the direction in which the pericardium B is separated from the optical member 7. By doing so, as shown in FIG. 8B, it is possible to dispose the wire 3 so that the angle β becomes greater than the angle α.

The upward movement of the wire 3 is achieved by lifting up the entire endoscope sheath 1 toward the pericardium B by moving the access sheath 4 toward the pericardium B. Alternatively, the upward movement of the wire 3 may be achieved by bending the bending portion 4*a* of the access sheath 4 or by bending the bending portions 1*a* and 1*b* of the endoscope sheath 1.

FIG. 9 shows examples of design values of the endoscope system 100 and observation conditions therefor. In this design example, the angle α is 36°. As the wire 3, a general guide wire having an outer diameter of 0.37 mm to 0.89 mm is used.

Figure 8B:
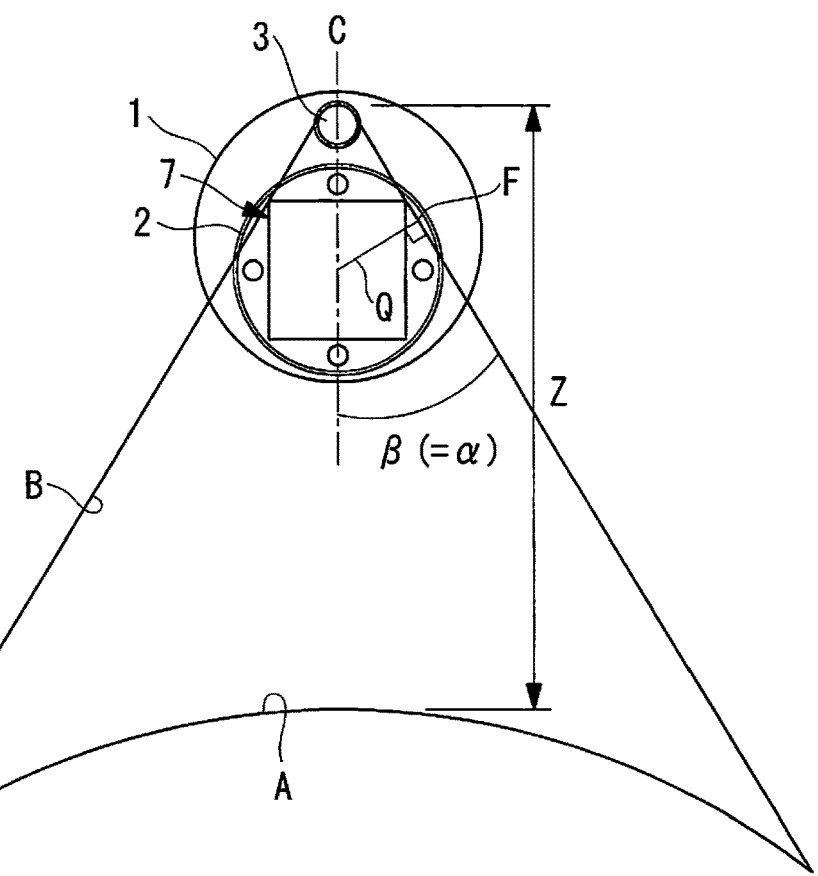
FIG. 8B is a diagram for explaining the wire placing step, and is a front view of the endoscope sheath and the endoscope disposed between the heart and the pericardium.
Figure 8C:
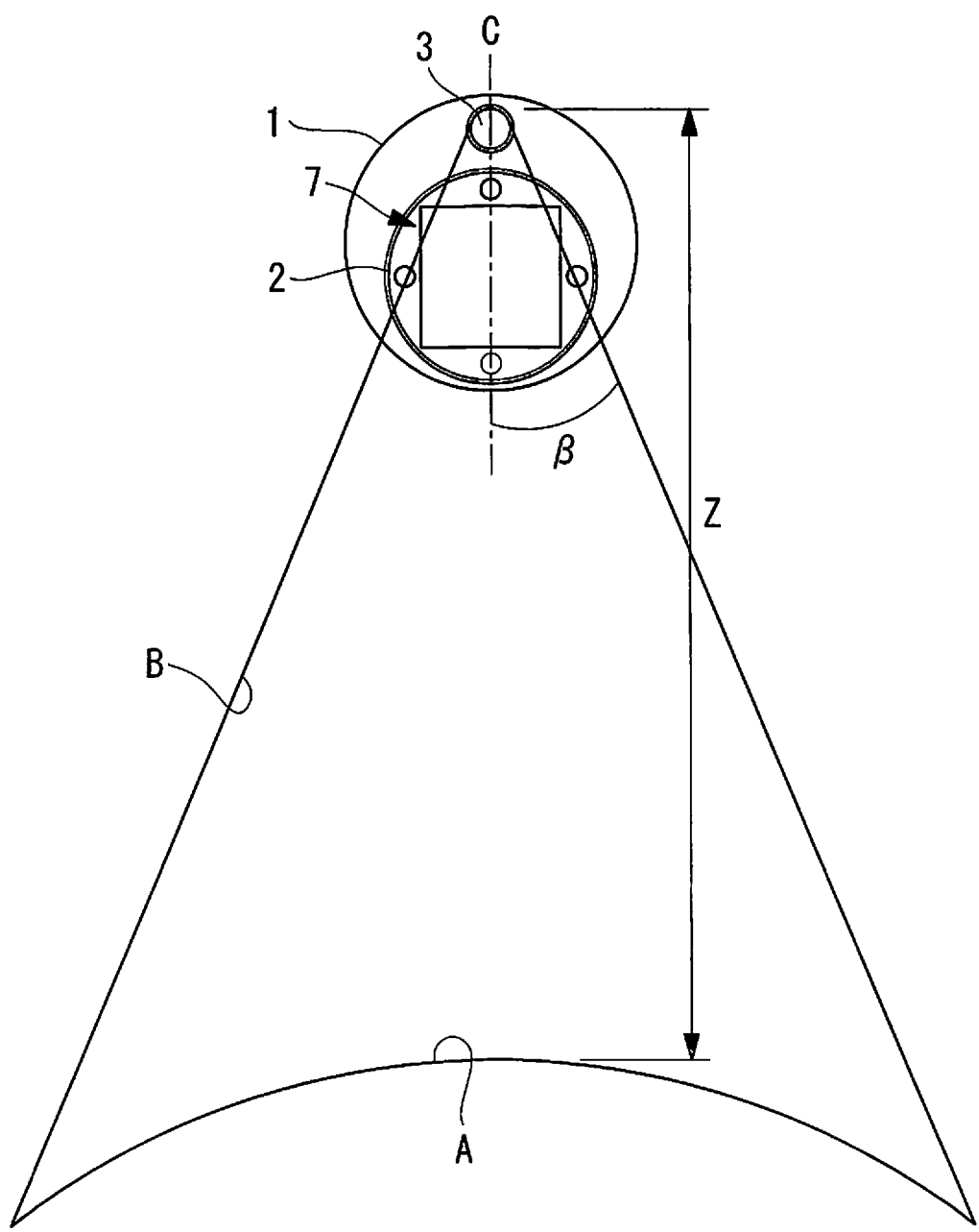
FIG. 8C is a diagram for explaining the wire placing step, and is a front view of the endoscope sheath and the endoscope disposed between the heart and the pericardium.

In the case in which the heart A having a diameter φ of 100 mm is observed by means of the endoscope 2 by using the thinnest guide wire (W=0.37 mm), as shown in FIG. 8B, when the maximum distance Z between the heart A and the pericardium B (the distance between the heart A and an end of the wire 3 on the pericardium B side in a direction parallel to a perpendicular line drawn from the center of the wire 3 to the surface of the heart A) is 20 mm, the angle β between the centerline C and the tangent T2 of the pericardium B is 46°. As shown in FIG. 8C, when the maximum distance Z between the heart A and the pericardium B becomes equal to or greater than 35 mm, the angle β becomes equal to or less than 36°, and the pericardium B covers the area in front of the optical member 7.

In the case in which the heart A is observed under the condition of the maximum distance Z=20 mm by using the thinnest guide wire (W=0.37 mm), when the diameter φ of the heart A becomes equal to or less than 58 mm, the angle β becomes equal to or less than 36°, and the pericardium B covers the area in front of the optical member 7.

Therefore, in the wire placing step, the wire 3 is disposed so that the angles β on the left and right sides of the centerline C become greater than 36°, and the distance Z becomes less than 35 mm.

Next, in the observing step, by making the distal-end surface of the endoscope 2 face the heart A by bending the bending portion 8 downward, it is possible to perform a bird's-eye-view observation of the observation target site in the heart A.

As has been described above, in the case in which the wire 3 having a diameter that is smaller than that of the optical member 7, such as a guide wire, is used as the member for lifting up the pericardium B, the width of a space S in the left-to-right direction becomes smaller than the width L of the optical member 7, and, in some cases, the pericardium B covers both end portions on the left and right sides of the optical member 7. In a state in which the pericardium B covers the end portions of the optical member 7, the illumination light emitted from the illumination lenses 7a is blocked by the pericardium B and does not reach the observation target site or a portion of a viewing field of the objective lens 7b is blocked by the pericardium B, thus interfering with the observation of the heart A.

With this embodiment, by disposing the wire 3 so that the angle $\beta$ becomes greater than the angle $\alpha$, it is possible to lift up the pericardium B by means of the wire 3 so as not to cover the optical member 7, and a space S that is larger than the width L of the optical member 7 is ensured in the area in front of the optical member 7. By doing so, it is possible to observe the heart A by means of the endoscope 2 without being interfered with by the pericardium B.

In the wire placing step or the observing step, it is preferable that a protrusion length Y from the distal-end surface of the objective lens 7b at the distal end of the endoscope 2 to the distal end of the wire 3 be controlled so as to be equal to or greater than a maximum value V of an object-distance at which it is possible to observe the surface of the heart A by means of the objective lens 7b (maximum object distance).

Figure 10A:
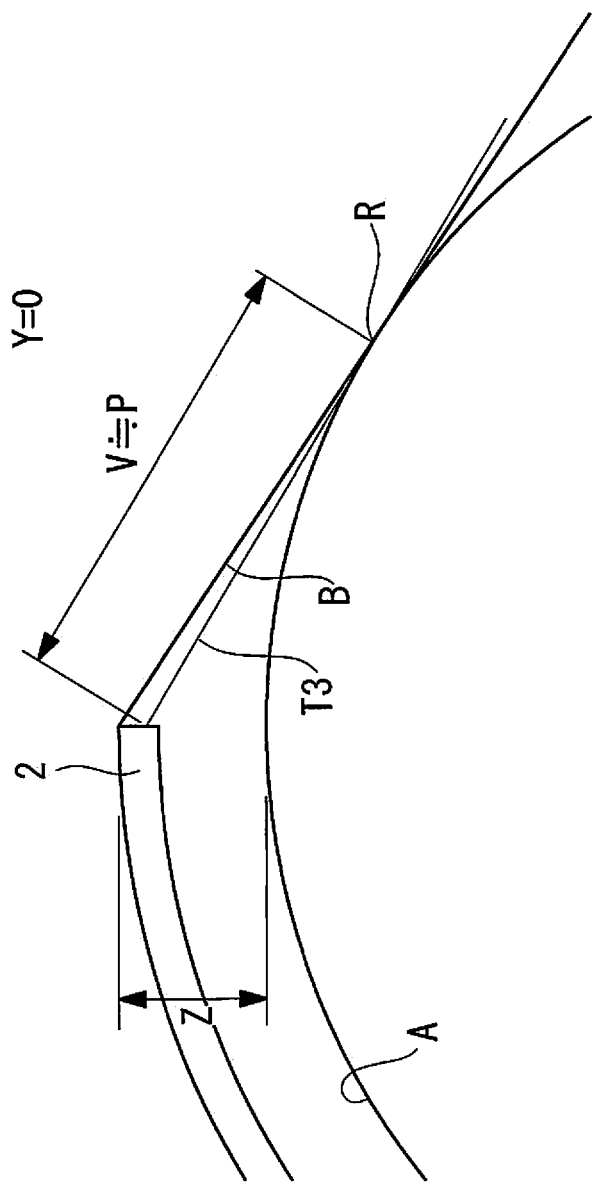
FIG. 10A is a diagram for explaining the relationship between a maximum object distance and a protrusion length of the wire.
Figure 10C:
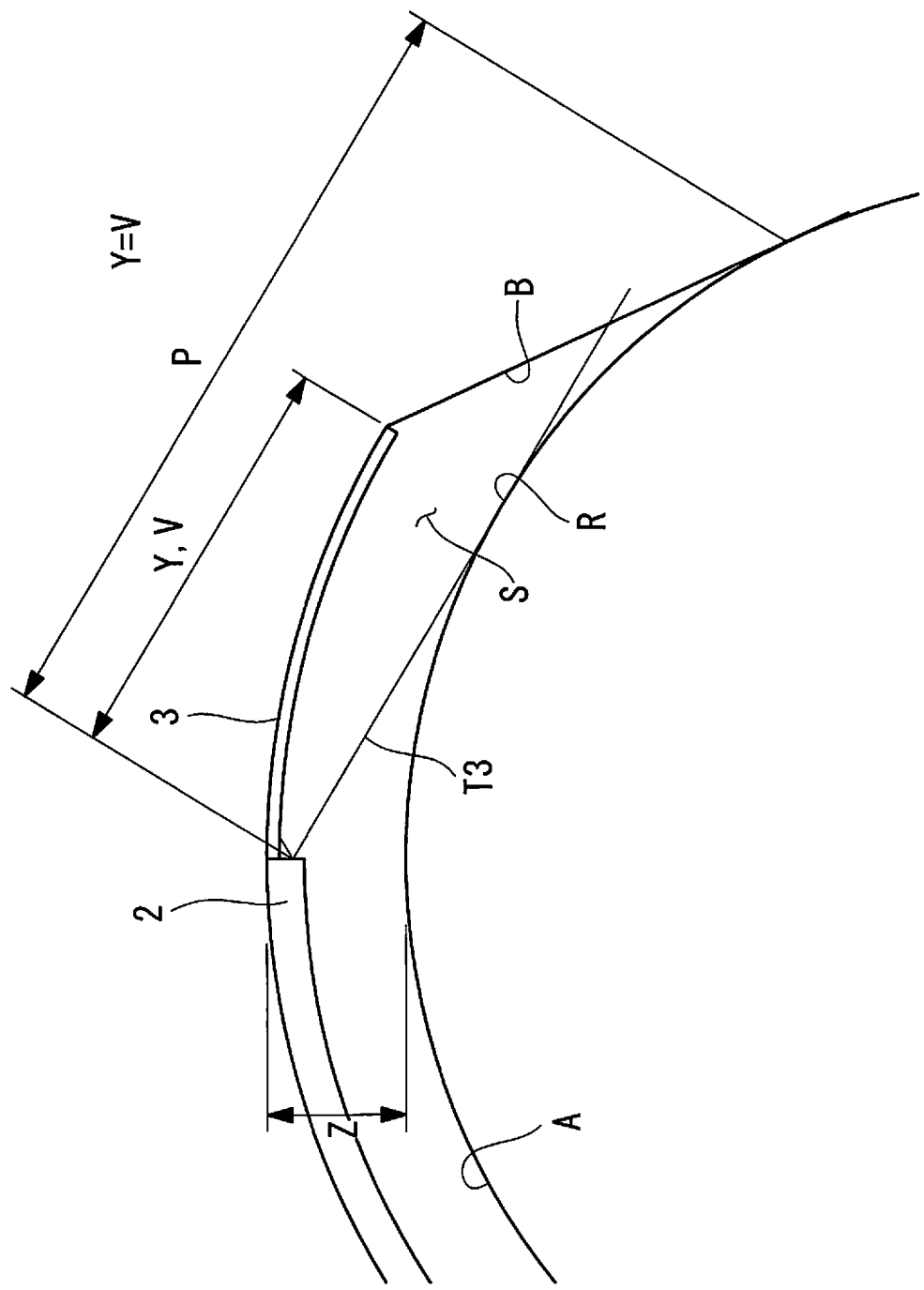
FIG. 10C is a diagram for explaining the relationship between the maximum object distance and the protrusion length of the wire.

As shown in FIGS. 10A to 10C, the maximum object distance V is a distance in a direction parallel to a tangent T3 between the distal-end surface of the objective lens 7b and a contact point R. Among tangents of the surface of the heart A in a plane that includes the optical axis of the objective lens 7b, the tangent T3 is a tangent that passes through the center of the distal-end surface of the objective lens 7b. The contact point R is a point at which the tangent T3 comes into contact with the surface of the heart A. Although it is possible to observe, by means of the objective lens 7b, the surface of the heart A in an area that is closer to the objective lens 7b than the contact point R is, it is not possible to observe, by means of the objective lens 7b, the surface of the heart A in an area farther away from the objective lens 7b than the contact point R is.

As shown in FIG. 10A, when the protrusion length Y of the wire 3 is 0 mm, the maximum object distance V in the viewing field becomes substantially equal to a maximum distance P in the direction parallel to the tangent T3 of the space S ensured in the pericardial cavity.

As shown in FIG. 10B, with an increase in the protrusion length Y of the wire 3, the space S increases in the depth direction of the viewing field, thus increasing the maximum distance P. Therefore, it is possible to dispose a treatment tool or the like in the space S. However, in the case in which the protrusion length Y is less than the maximum object distance V, the distance between the heart A and the pericardium B becomes smaller at a position separated from the objective lens 7b.

As shown in FIG. 10C, when the protrusion length Y of the wire 3 is equal to or greater than the maximum object distance V in the viewing field, it is possible to ensure a sufficient space S over the entire area in which the surface of the heart A can be observed by means of the objective lens 7b.

The maximum object distance V in the viewing field varies in accordance with the observation conditions (parameters Z and $\phi$).

FIGS. 10A to 10C show examples of observation conditions that are assumed in the case in which the diameter $\phi$ of the heart is at a maximum ($\phi$=200 mm), and Z=20 mm. With these observation conditions, the maximum object distance V in the viewing field is approximately 62 mm. Therefore, it is preferable that the protrusion length Y be equal to or greater than 62 mm.

It is permissible to provide a means for restricting the length by which the distal-end portion of the wire 3 protrudes from the distal-end opening 6a and the length by which the distal-end portion of the endoscope 2 protrudes from the distal-end opening 5a so that the protrusion length Y of the wire 3 becomes equal to or greater than the maximum object distance V.

Figure 11A:
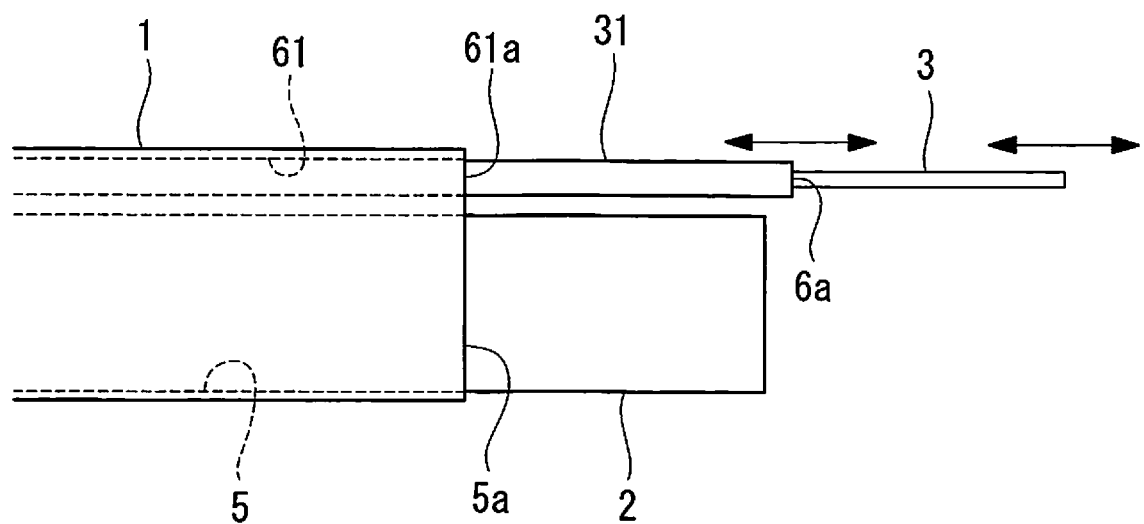
FIG. 11A is a side view of a distal-end portion of the endoscope system showing a modification of a protruding portion.
Figure 11B:
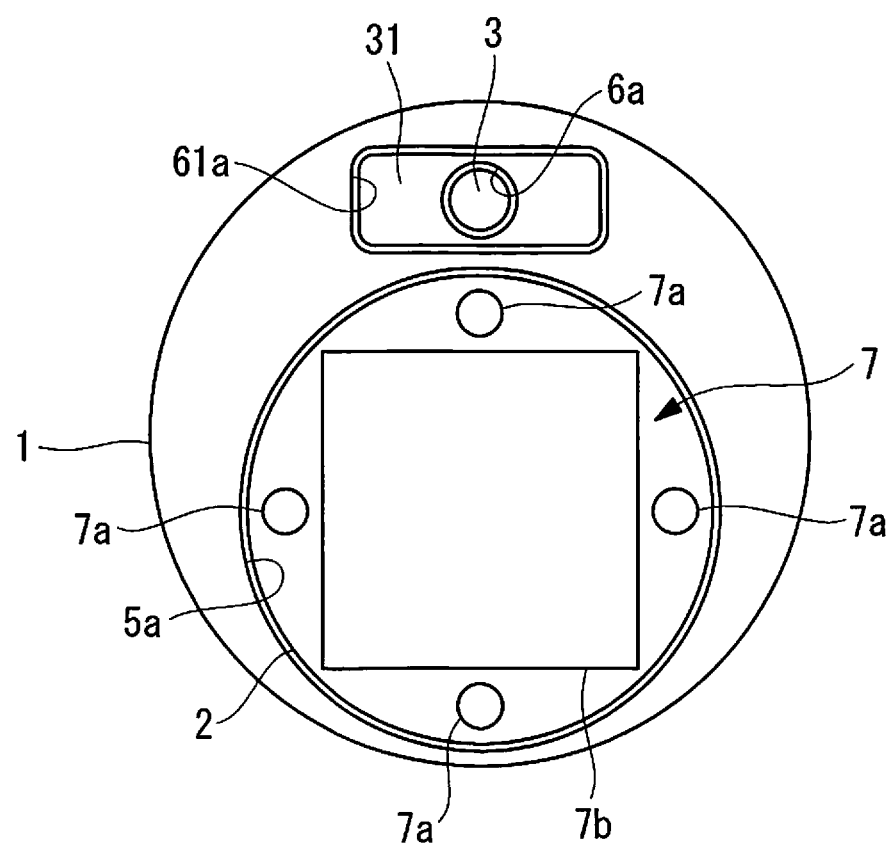
FIG. 11B is a front view as viewed from a distal-end side of the endoscope system in FIG. 11A.

In this embodiment, although the protruding portion is assumed to be the wire 3 that is protrudable from and retractable into the opening 6a in the distal-end surface of the endoscope sheath 1, alternatively, as shown in FIGS. 11A and 11B, a hood 31 that serves as a first protruding portion that is protrudable from and retractable into the distal-end surface of the endoscope sheath 1 may be provided, and the wire 3 that serves as a second protruding portion may be protrudable from and retractable into the distal end of the hood 31.

The hood 31 is an elongated columnar member that has a width W that is smaller than the width L of the optical member 7 in the left-to-right direction. The endoscope sheath 1 is provided with a lumen 61 that passes through the endoscope sheath 1 in the longitudinal direction and in which the hood 31 is disposed along the longitudinal direction, and a distal-end opening (opening portion) 61a of the lumen 61 is provided in the distal-end surface of the endoscope sheath 1. The hood 31 is provided with the lumen 6 that passes through the hood 31 in the longitudinal direction and in which the wire 3 is disposed along the longitudinal direction. The wire 3 is, for example, a guide wire that possesses a high flexibility and that has a diameter of approximately 0.37 mm, and the hood 31 possesses a rigidity that is greater than that of the wire 3.

The operator can make the distal-end portion of the hood 31 protrude from and retract into the distal-end opening 61a by pushing and pulling, in the longitudinal direction, the base-end portion of the hood 31 that is pulled outside the endoscope sheath 1 from the base-end opening of the lumen 61. In addition, the operator can make the distal-end portion of the wire 3 protrude from and retract into the distal-end opening 6a by pushing and pulling, in the longitudinal direction, the base-end portion of the wire 3 that is pulled outside the hood 31 from the base-end opening of the lumen 6.

With this modification, it is possible to separately use the hood 31 and the wire 3 having rigidities and widths that are different from each other depending on the situation. For example, by guiding the endoscope sheath 1 and the endoscope 2 to the observation target site along the wire 3 having high flexibility, and, subsequently, by ensuring a sufficient space S by making the hood 31 protrude, it is possible to make it easier to guide the endoscope 2 to the observation target site in the pericardial cavity, and it is possible to enhance the stability of the space S.

The hood 31 may be secured to the distal-end surface of the endoscope sheath 1, and the wire 3 may be protrudable from and retractable into the distal end of the secured hood 31.

In this embodiment, the endoscope system 100 may additionally be provided with a surgery assistance apparatus that assists rotational manipulation of the endoscope 2 by the operator in the wire placing step.

Figure 12A:
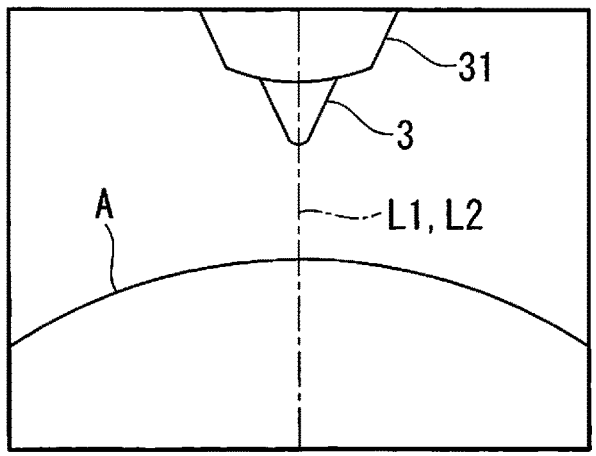
FIG. 12A is a diagram showing an example of an endoscope image that a surgery assistance apparatus displays on a monitor.
Figure 12B:
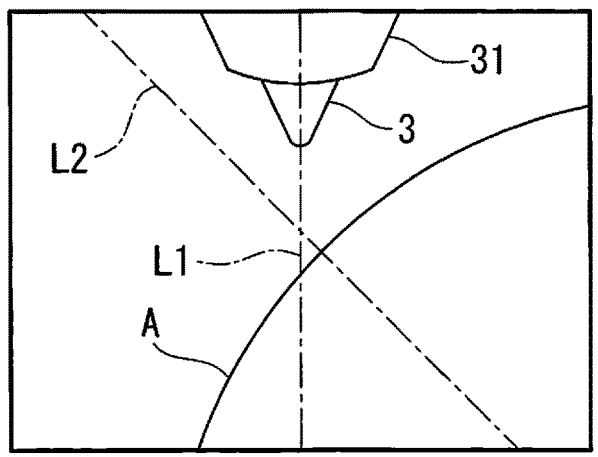
FIG. 12B is a diagram showing another example of the endoscope image that the surgery assistance apparatus displays on the monitor.
Figure 12C:
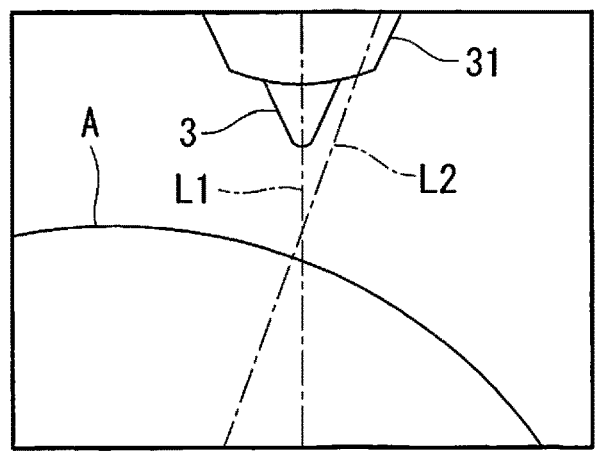
FIG. 12C is a diagram showing another example of the endoscope image that the surgery assistance apparatus displays on the monitor.

The surgery assistance apparatus receives the endoscope images from the endoscope 2, performs real-time processing of the received endoscope images, and, as shown in FIGS. 12A to 12C, an endoscope image in which two lines L1 and L2 are superimposed is displayed on the monitor. The line L1 is an extension of the longitudinal axes of the protruding portions 3 and 31 in the endoscope image, and is a line that passes through the center of the endoscope image. The line L2 is a normal line of the outline of the heart A in the endoscope image, and is a line that passes through the center of the endoscope image. This kind of processing is executed by, for example, a processor such as a CPU (central processing unit) built into the surgery assistance apparatus.

FIG. 12A shows a state in which the pericardium B, the protruding portions 3 and 31, the optical member 7, and the heart A are arranged in this order in the top-to-bottom direction of the endoscope 2, and the line L1 and the line L2 are aligned with each other. FIG. 12B shows a state in which the endoscope 2 is rotated clockwise with respect to the heart A. FIG. 12C shows a state in which the endoscope 2 is rotated counterclockwise with respect to the heart A.

In the wire placing step, the operator rotates the endoscope sheath 1 and the endoscope 2 so that the line L1 and the line L2 extend in the top-to-bottom direction of the endoscope image and are aligned with each other. By doing so, the operator disposes the endoscope 2 and the wire 3 in the state shown in FIG. 12A, and thus, he/she can maximize the area in the heart A observed by means of the objective lens 7b. The surgery assistance apparatus may output a sound that indicates the direction in which the endoscope 2 is rotated instead of displaying the lines L1 and L2 or in addition thereto. For example, in the case of the example in FIG. 12B, the surgery assistance apparatus may output the speech, "please rotate the endoscope counterclockwise by 45°".

In the observing step, the operator does not necessarily need to align the line L1 with the line L2, and he/she may rotate the endoscope 2 within a predetermined rotational angle range in which the relationship that the angle $\beta$ is greater than the angle $\alpha$ is maintained with respect to the state in which the line L1 is aligned with the line L2 (rotational angle 0°). The predetermined rotational angle range varies in accordance with the observation conditions (parameters W, X, L, Z, and $\phi$), and the predetermined rotational angle range becomes greater with an increase in the diameter $\phi$ of the heart A.

Figure 13A:
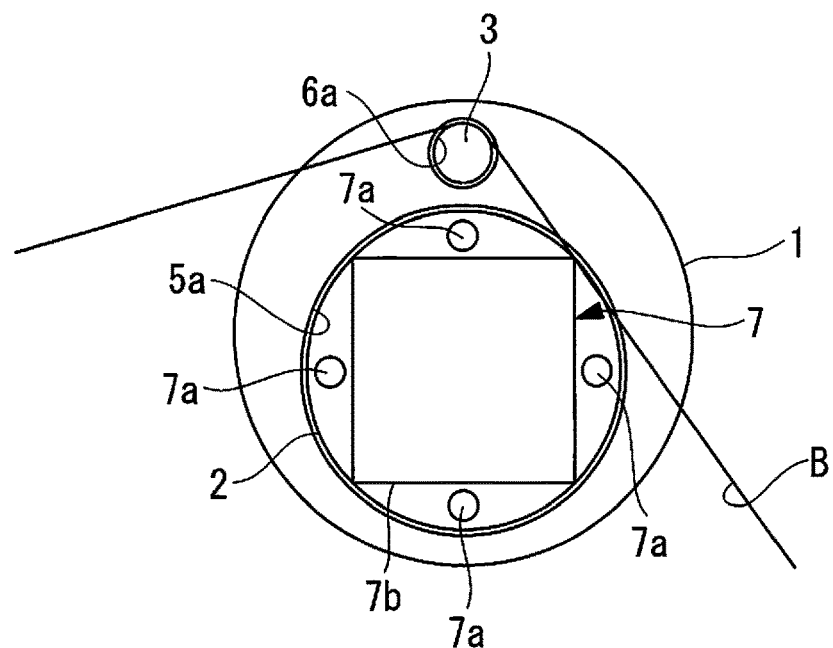
FIG. 13A is a diagram showing an example of a rotating motion of the endoscope in an observing step.
Figure 13B:
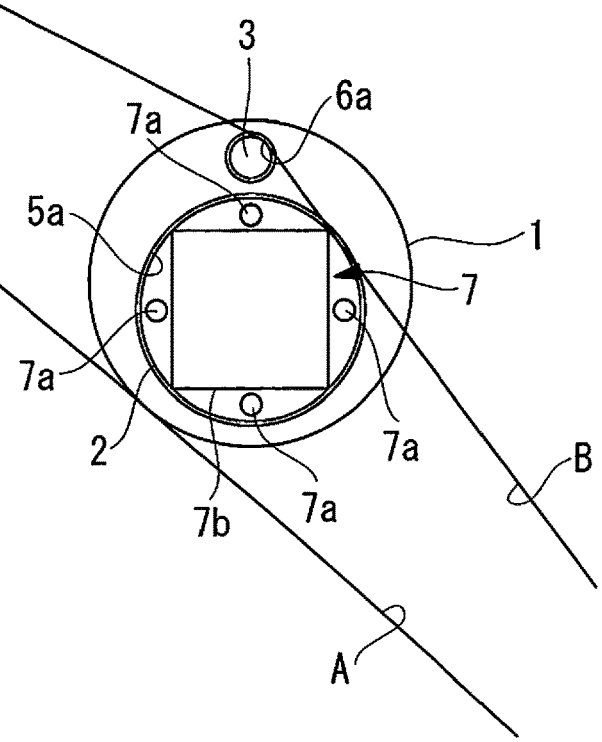
FIG. 13B is a diagram showing another example of the rotating motion of the endoscope in the observing step.

FIGS. 13A and 13B show examples of design values of the endoscope system 100 and examples of observation conditions for the case in which the diameter $\phi$ of the heart A is at the maximum ($\phi$=200 mm). With regard to other parameters, W=0.37 mm, X=0.15 mm, and L=2.0 mm.

FIG. 13A shows a state in which the distal end of the endoscope sheath 1 is lifted up to a position at which the endoscope sheath 1 is separated from the heart A (Z=20 mm). With these observation conditions, the operator may rotate the endoscope 2 within a range of ±18°.

FIG. 13B shows a state in which the distal end of the endoscope sheath 1 is disposed on the heart A in contact with the heart A, and indicates, among the assumed observation conditions, observation conditions with which the predetermined rotational angle range reaches a maximum. With these observation conditions, the operator may rotate the endoscope 2 within a range of ±40°. Therefore, in the wire placing step and the observing step, the acceptable maximum rotational angle is ±40°.

In this embodiment, although the endoscope sheath 1 and the endoscope 2 are assumed to be separate components, the endoscope sheath 1 and the endoscope 2 in the lumen 5 may be secured to each other.

In this case, the endoscope 2 is positioned in the longitudinal direction with respect to the endoscope sheath 1 so that the bending portion 8 protrudes outside the endoscope sheath 1 from the distal-end opening 5a, and is positioned about the longitudinal axis with respect to the endoscope sheath 1 so that the bottom direction of the endoscope 2 is aligned with the bottom direction of the endoscope sheath 1. The endoscope 2 is secured to the endoscope sheath 1 in a state in which the endoscope 2 is positioned in this way. By doing so, in the inserting step, when the orientation of the endoscope 2 is adjusted so that, in the endoscope image, the heart A is disposed on the lower side and the pericardium B is disposed on the upper side, the wire 3 is naturally disposed closer to the pericardium B than the optical member 7 is. Therefore, it is not necessary to adjust the relative orientations of the endoscope sheath 1 and the endoscope 2 in the wire placing step.

The following aspects of the invention are derived from the above-described embodiment and modifications thereof.

An aspect of the present invention is a pericardial-cavity observing method using an endoscope system provided with a tubular, long endoscope sheath that has a lumen that passes therethrough in a longitudinal direction and that has a first radial direction and a second radial direction that are orthogonal to each other, a protruding portion that is disposed on one side of a distal-end opening of the lumen in the first radial direction and that protrudes from a distal-end surface of the endoscope sheath in the longitudinal direction, and an endoscope that has, at a distal end thereof, an optical member for observing an imaging subject and that is disposed in the lumen in a longitudinal direction thereof, wherein the protruding portion has a width that is smaller than that of the optical member in the second radial direction, the pericardial-cavity observing method including: a step of inserting the endoscope sheath and the endoscope into a space between a heart and a pericardium; a step of disposing the protruding portion closer to the pericardium than the optical member is; and a step of observing the heart by means of the endoscope, wherein, in the step of disposing the protruding portion, the protruding portion is disposed so that an angle that is formed between a centerline that passes through a center of the protruding portion and a center of the optical member and a tangent of the pericardium that passes through a foot of a perpendicular line drawn, from the center of the optical member, to the pericardium sagging down from the protruding portion toward the heart becomes greater than an angle formed between the centerline and an external common tangent of the protruding portion and the optical member.

With this aspect, after inserting the endoscope sheath and the endoscope into the space between the heart and the pericardium, by disposing the protruding portion that protrudes from the distal-end surface of the endoscope sheath closer to the pericardium than the optical member is, the pericardium is lifted up by means of the protruding portion in the area in front of the distal-end surface of the endoscope sheath in a direction in which the pericardium is separated from the heart. By doing so, a sufficient space is ensured in the area in front of the distal-end surface of the endoscope sheath. Therefore, by making the endoscope in the lumen protrude from the distal-end opening so that the distal-end surface of the endoscope is disposed in the space between the protruding portion and the heart, it is possible to observe the heart in the pericardial cavity.

In this case, because the width of the protruding portion is smaller than the width of the optical member, the width of the space becomes smaller than the width of the optical member on the side closer to the protruding portion, and, in some cases, the pericardium sagging down from the protruding portion toward the heart covers the area in front of the optical member.

Therefore, by disposing the protruding portion so that the angle formed between the centerline and the tangent of the pericardium becomes greater than the angle formed between the centerline and the external common tangent of the protruding portion and the optical member, the pericardium sagging down from the protruding portion toward the heart is disposed at a position at which the pericardium does not cover the area in front of the optical member. By doing so, it is possible to reliably ensure a sufficient space for observing the heart by means of optical members such as illumination lenses and an objective lens while using a small-diameter protruding portion.

In the above-described aspect, a spacing between the optical member and the protruding portion in the first radial direction may be equal to or greater than 0.15 mm, a width of the protruding portion in the second radial direction may be equal to or greater than 0.3 mm, a width of the optical member in the second radial direction may be equal to or greater than 2 mm, and, in the step of disposing the protruding portion, the protruding portion may be disposed so that the angle between the tangent of the pericardium and the centerline becomes greater than 36°, and so that a distance between the heart and the protruding portion becomes less than 35 mm.

In the case in which such a small-diameter endoscope system is used, by providing the protruding portion, as described above, it is possible to dispose the pericardium lifted up by the protruding portion at a position at which the pericardium does not cover the area in front of the optical member.

In the above-described aspect, in the step of observing the heart, the protruding portion may be disposed so that a protrusion length from the optical member at a distal end of the endoscope to a distal end of the protruding portion becomes equal to or greater than a maximum object distance at which a surface of the heart can be observed by means of the optical member, for example, 62 mm or greater.

By doing so, it is possible to ensure a sufficient space over the entire region of the surface of the heart that can be observed by means of the optical member.

In the above-described aspect, the endoscope sheath may have an opening portion provided in the distal-end surface, the protruding portion may be protrudable from and retractable into the opening portion in the longitudinal direction, and, in the step of disposing the protruding portion, the protruding portion may be made to protrude from the opening portion, and a distal end of the protruding portion may be disposed at a position at which the distal end of the protruding portion protrudes from the distal-end surface of the endoscope sheath farther out than the optical member at the distal end of the endoscope is. The protruding portion may be a wire.

By doing so, it is possible to accommodate the protruding portion inside the endoscope sheath when the protruding portion is not needed.

In the above-described aspect, the endoscope system may be provided with: a tubular access sheath into which the endoscope sheath is inserted along a longitudinal direction thereof; and a rotation-stopping mechanism that restricts rotation of the endoscope about a longitudinal axis thereof in the access sheath, wherein, in the step of observing the heart, rotation of the endoscope may be restricted by means of the rotation-stopping mechanism so that, in an endoscope image acquired by using the optical member, the heart is disposed on a lower side and the pericardium is disposed on an upper side.

By doing so, by restricting the rotation of the endoscope by means of the rotation-stopping mechanism after adjusting the orientation of the endoscope about the longitudinal axis thereof between the heart and the pericardium, it is possible to prevent the endoscope from being unintentionally rotated.

In the above-described aspect, the endoscope system is provided with: a monitor on which an endoscope image acquired by using the endoscope is displayed; and a surgery assistance apparatus that superimposes, on the endoscope image, a first line that is an extension of a longitudinal axis of the protruding portion in the endoscope image and that passes through a center of the endoscope image, and a second line that is a normal line of an outline of the heart in the endoscope image and that passes through the center of the endoscope image, wherein, in the step of disposing the protruding portion, the endoscope sheath and the endoscope may be rotated so that, in the endoscope image, the first line and the second line are extended in a top-to-bottom direction and aligned with each other.

By doing so, it is possible to assist rotational manipulations of the endoscope sheath and the endoscope performed by the operator.

In the above-described aspect, in the step of observing the heart, the endoscope may be rotated within a range of ±40° with respect to a state in which the first line and the second line are extended in the top-to-bottom direction and aligned with each other.

By doing so, it is possible to change the orientation of the endoscope with respect to the heart while holding the pericardium at a position at which the pericardium does not cover the area in front of the optical member.

REFERENCE SIGNS LIST 1 endoscope sheath
2 endoscope
3 wire (protruding portion)
31 hood (protruding portion)
4 access sheath
5, 6 lumen
5a, 6a distal-end opening
7 optical member
7a illumination lens
7b objective lens
8 bending portion
9 securing device (rotation-stopping mechanism)
10a protrusion (rotation-stopping mechanism)
10b groove (rotation-stopping mechanism)
100 endoscope system
A heart
B pericardium

The invention claimed is:

1. A pericardial-cavity observing method using an endoscope system provided with a tubular elongated endoscope sheath that has a lumen that passes therethrough in a longitudinal direction and that has a first radial direction and a second radial direction that are orthogonal to each other, a protruding portion that is disposed on one side of a distal-end opening of the lumen in the first radial direction and that protrudes from a distal-end surface of the endoscope sheath in the longitudinal direction, and an endoscope that has, at a distal end thereof, an optical member for observing an imaging subject and that is disposed in the lumen in a longitudinal direction thereof, wherein the protruding portion has a width that is smaller than that of the optical member in the second radial direction, the pericardial-cavity observing method comprising:

a step of inserting the endoscope sheath and the endoscope into a space between a heart and a pericardium;

a step of disposing the protruding portion closer to the pericardium than the optical member is; and a step of observing the heart by means of the endoscope, wherein, in the step of disposing the protruding portion, the protruding portion is disposed so that an angle that is formed between a centerline that passes through a center of the protruding portion and a center of the optical member and a tangent of the pericardium that passes through a foot of a perpendicular line drawn, from the center of the optical member, to the pericardium sagging down from the protruding portion toward the heart becomes greater than an angle formed between the centerline and an external common tangent of the protruding portion and the optical member.

2. The pericardial-cavity observing method according to claim 1, wherein a spacing between the optical member and the protruding portion in the first radial direction is equal to or greater than 0.15 mm, a width of the protruding portion in the second radial direction is equal to or greater than 0.3 mm, a width of the optical member in the second radial direction is equal to or greater than 2 mm, and, in the step of disposing the protruding portion, the protruding portion is disposed so that the angle that is formed between the tangent of the pericardium and the centerline becomes greater than 36°, and so that a distance between the heart and the protruding portion becomes less than 35 mm.

3. The pericardial-cavity observing method according to claim 1, wherein the optical member includes an illumination lens.

4. The pericardial-cavity observing method according to claim 1, wherein the optical member includes an objective lens.

5. The pericardial-cavity observing method according to claim 2, wherein, in the step of observing the heart, the protruding portion is disposed so that a protrusion length from the optical member at a distal end of the endoscope to a distal end of the protruding portion becomes 62 mm or greater.

6. The pericardial-cavity observing method according to claim 2, wherein, in the step of observing the heart, the protruding portion is disposed so that a protrusion length from the optical member at a distal end of the endoscope to a distal end of the protruding portion becomes equal to or greater than a maximum object distance at which a surface of the heart can be observed by means of the optical member.

7. The pericardial-cavity observing method according to claim 1, wherein the endoscope sheath has an opening portion provided in the distal-end surface, the protruding portion is protrudable from and retractable into the opening portion in the longitudinal direction, and, in the step of disposing the protruding portion, the protruding portion is made to protrude from the opening portion, and a distal end of the protruding portion is disposed at a position at which the distal end of the protruding portion protrudes from the distal-end surface of the endoscope sheath farther out than the optical member at the distal end of the endoscope is.

8. The pericardial-cavity observing method according to claim 7, wherein the protruding portion is a wire.

9. The pericardial-cavity observing method according to claim 1, wherein the endoscope system is provided with:

a tubular access sheath into which the endoscope sheath is inserted along a longitudinal direction thereof; and a rotation-stopping mechanism that restricts rotation of the endoscope about a longitudinal axis thereof in the access sheath, and wherein, in the step of observing the heart, rotation of the endoscope is restricted by means of the rotation-stopping mechanism so that, in an endoscope image acquired by using the optical member, the heart is disposed on a lower side and the pericardium is disposed on an upper side.

10. The pericardial-cavity observing method according to claim 1, wherein the endoscope system is provided with:

a monitor on which an endoscope image acquired by using the endoscope is displayed; and a surgery assistance apparatus that superimposes, on the endoscope image, a first line that is an extension of a longitudinal axis of the protruding portion in the endoscope image and that passes through a center of the endoscope image, and a second line that is a normal line of an outline of the heart in the endoscope image and that passes through the center of the endoscope image, wherein, in the step of disposing the protruding portion, the endoscope sheath and the endoscope are rotated so that, in the endoscope image, the first line and the second line are extended in a top-to-bottom direction and aligned with each other.

11. The pericardial-cavity observing method according to claim 10, wherein, in the step of observing the heart, the endoscope is rotated within a range of ±40° with respect to a state in which the first line and the second line are extended in the top-to-bottom direction and aligned with each other.

* * * * *